United States Patent [19]
Mayol et al.

[11] Patent Number: 5,256,664
[45] Date of Patent: Oct. 26, 1993

[54] ANTIDEPRESSANT 3-HALOPHENYLPIPERAZINYLPROPYL DERIVATIVES OF SUBSTITUTED TRIAZOLONES AND TRIAZOLDIONES

[75] Inventors: Robert F. Mayol, Durham, Conn.; George M. Luke, LaFayette, N.Y.

[73] Assignee: Bristol-Myers Squibb Company, New York, N.Y.

[21] Appl. No.: 875,044

[22] Filed: Apr. 28, 1992

[51] Int. Cl.$^5$ .................. A61K 31/495; C07D 403/06
[52] U.S. Cl. .................................... 514/252; 544/366; 548/263.2; 549/450
[58] Field of Search .................. 544/366; 514/252

[56] References Cited

U.S. PATENT DOCUMENTS

| | | | |
|---|---|---|---|
| 4,338,317 | 7/1982 | Temple et al. | 514/255 |
| 4,386,091 | 5/1983 | Temple, Jr. et al. | 544/366 |
| 4,487,773 | 12/1984 | Temple, Jr. et al. | 544/295 |
| 4,613,600 | 9/1986 | Gammans et al. | 514/252 |

*Primary Examiner*—Emily Bernhardt
*Attorney, Agent, or Firm*—Richard P. Ryan

[57] ABSTRACT

2-(3-[4-(3-Halophenyl)-1-piperazinyl]propyl derivatives of certain 4-alkyl- or 4-phenoxyalkyl-2,4-dihydro-3H-1,2,4-triazol-3-ones and triazol-3,5-diones are psychotropic agents having promise as antidepressants by virtue of their receptor site binding affinity profiles and animal pharmacology.

14 Claims, No Drawings

ANTIDEPRESSANT 3-HALOPHENYLPIPERAZINYLPROPYL DERIVATIVES OF SUBSTITUTED TRIAZOLONES AND TRIAZOLDIONES

BACKGROUND OF THE INVENTION

The present invention relates to 1,2,4-triazole heterocyclic carbon compounds, their preparation, metabolic transformations and use. More particularly, the invention relates to keto and triazoldione analogs of the antidepressant agent nefazodone.

Nefazodone is a member of a series of compounds having structure (1) as disclosed by Temple, Jr., et al. in U.S. Pat. No. 4,338,317.

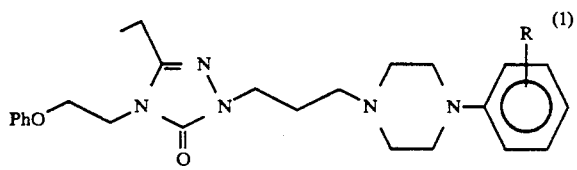

Nefazodone (R is meta-chloro) has been extensively studied clinically as an antidepressant agent.

A major metabolic pathway for nefazodone and related analogs involves α-carbon hydroxylation of the ethyl group attached to the 5-position of the triazolone ring. These antidepressant compounds as well as certain ether and ester derivatives were disclosed and claimed in U.S. Pat. No. 4,613,600 as structure (2). In these compounds, Z is

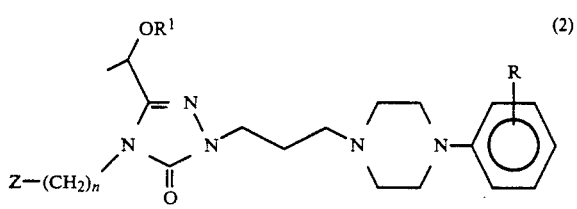

hydrogen or phenoxy and $R^1$ is, inter alia, an alkyl or acyl moiety.

SUMMARY AND DETAILED DESCRIPTION OF THE INVENTION

The present invention concerns compounds of Formula I and their acid addition salts and/or hydrates.

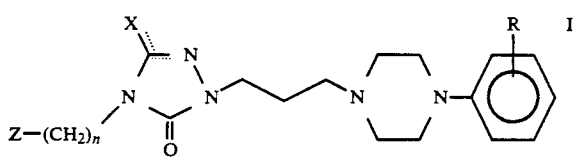

In the foregoing structural formula the symbol R denotes halogen, preferably chloro, and trifluoromethyl; Z is hydrogen and

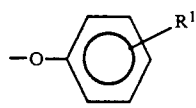

with $R^1$ being hydrogen, halogen, $C_{1-4}$ alkoxy and trifluoromethyl; and n is an integer from 2-4. The symbol X is either an oxygen atom, providing a carbonyl moiety; or is an acetyl group. The single and dotted lines represent either a covalent single bond or a double bond. The compounds of Formula I exist then in two structural subclasses, Ia and Ib.

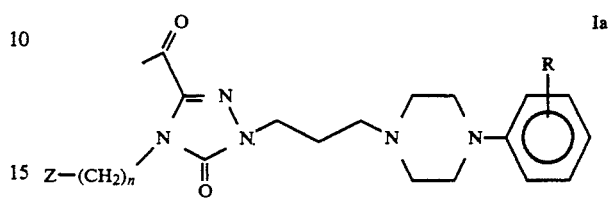

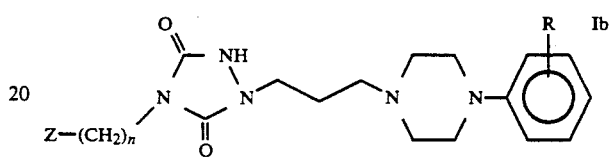

Compounds of formula I arose from investigations of the metabolism of the antidepressant drug nefazodone. Blood levels of a new and uncharacterized major metabolite of nefazodone were observed following nefazodone administration to humans and animals (rat and dog). No indication of this circulating metabolite had been seen in urine or bile samples. Subsequently, this new major metabolite was isolated and identified as having the following structure:

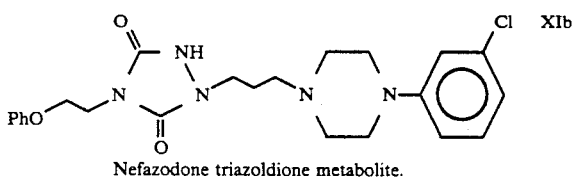

Nefazodone triazoldione metabolite.

In its broadest aspect, the instant invention is concerned with structural variation at the 5-position of the 3H-1,2,4-triazol-3-one ring of nefazodone and its related analogs. The compounds of the present invention are characterized by replacement of the 5-ethyl-group by an acetyl group (Ia) or by transformation of the 5-position to a carbonyl moiety (Ib). The invention also concerns the discovery that compounds of the present invention are psychotropic agents displaying selective central nervous system effects which are associated with useful antidepressant activity. The more preferred compounds of the present series have the structures of Formula XIb, and in the most preferred compounds of Formula XIb, Z is a phenoxy moiety.

For medicinal use, the pharmaceutically acceptable acid addition salts, those salts in which the anion does not contribute significantly to toxicity or pharmacological activity of the organic cation, are preferred. The acid addition salts are obtained either by reaction of an organic base of structure I with an inorganic or organic acid, preferably by contact in solution, or by any of the standard methods detailed in the literature and available to any practitioner skilled in the art. Examples of useful organic acids are carboxylic acids such as maleic acid, acetic acid, tartaric acid, propionic acid, fumaric acid, isethionic acid, succinic acid, pamoic acid, cyclamic acid, tannic acid, and the like; useful inorganic acids are hydrohalic acids such as HCl, HBr, HI; sulfuric acid, phosphoric acid; and the like.

The Formula I compounds are useful pharmacologic agents with psychotropic properties. In this regard they exhibit selective central nervous system effects which are associated with antidepressant activity. The effects are demonstrated by means of conventional in vitro binding characteristics in certain CNS receptor site test systems and in a selected in vivo model which has been shown to be correlative of the antidepressant activity associated with the structurally-related agents, nefazodone and its 5-hydroxyethyl metabolite.

Specifically, nefazodone triazoldione (XIb, "nef-triazoldione") was comparatively tested with nefazodone and the 5-hydroxyethyl metabolite ("OH-nefazodone"). Both of these agents possess useful antidepressant properties (Cf: U.S. Pat. No. 4,338,317 and U.S. Pat. No. 4,613,600). According to in vitro binding testing, nef-triazoldione displays affinity for serotonin receptors as does nefazodone and OH-nefazodone. Similarly, nef-triazoldione was relatively inactive with respect to dopamine receptor binding, cholinergic receptor binding, and alpha-receptor binding, in general these binding activities fall between those for nefazodone and OH-nefazodone. The binding of nef-triazoldione at serotonin type 2 receptors was not as robust as for both nefazodone and OH-nefazodone; however nef-triazoldione displayed lower affinity at alpha-receptor binding sites than the two reference compounds. The latter observation is significant in that agents with low affinity for alpha-receptors relative to serotonin type 2 receptors are less likely to elicit certain undesirable side effects, such as sedation and lowering of blood pressure. Thus nef-triazoldione, a representative of the instant XIb compounds, displayed a binding profile similar to related antidepressant agents.

The efficacy of nef-triazoldione at serotonin type 2 receptor sites in vivo was determined by examining its acute effect in a rat model based on the 5-HT$_2$-mediated DOI (chemically, 1-(2,5-dimethoxy-4-iodophenyl)-2-aminopropane)-induced headshake response. Cf: Bedard and Pycock, Neuropharmacology 16: 663–670 (1977). A modest inhibition of the DOI-induced headshake response was produced and in this regard the XIb compound appeared to be less potent than either nefazodone or OH-nefazodone in this in vivo test. These results were comparable to the in vitro binding potencies of the test compounds at serotonin type 2 receptors. Thus the in vivo results which correlate with selective in vitro binding are indicative of useful antidepressant effects following systemic administration of these compounds.

In regard to compounds of Formula Ia (5-acetyl-triazolones), experimental data indicate that they are metabolic precursors of Formula Ib triazoldione compounds. Using an in vitro human liver microsomal preparation with "keto-nefazodone" (Formula XIa) as substrate in a metabolite conversion experiment,

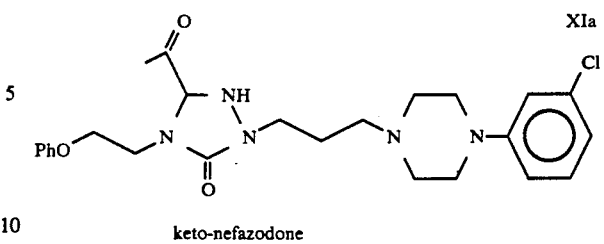

keto-nefazodone nefazodone triazoldione (XIb) was produced and isolated.

Examination of HPLC chromatographs of plasma from dogs given nefazodone shows small amounts of a compound with the same HPLC retention times as keto-nefazodone. The similarity of HPLC retention times for both keto-nefazodone and the parent drug nefazodone in many HPLC systems, as well as the small amount of the compound complicate the detection of this putative metabolite. As demonstrated with the in vitro liver enzyme experiments, Ia compounds may be expected to act as metabolic precursors for Ib compounds following systemic administration and portal circulation. As compound Ib precursors, Ia compounds inherently possess useful antidepression activity.

Another aspect then of the instant invention provides a method for treating a mammal afflicted with depression which comprises administering systemically to said mammal a therapeutically effective antidepressant amount of a compound of Formula I or a pharmaceutically acceptable acid addition salt thereof. The use and administration of the compounds of the instant invention is considered to be done in the same fashion as for the reference drugs nefazodone or trazodone. An effective antidepressant dose ranges from 1 to 40 mg/kg of body weight with a dosage dependent on effects sought, manner of administration, and to some extent with the particular Formula I compound selected. A preferred dosage range is 5 to 10 mg/kg body weight. Systemic administration refers to oral, sublingual, buccal, transdermal, transnasal, rectal, and parenteral (i.e. intramuscular, intravenous and subcutaneous). Generally it will be found that when a compound of the present invention is administered orally, a larger quantity of the active agent is required to produce the same effect as a smaller quantity given parenterally. In accordance with good clinical practice, it is preferred to administer the instant compounds at a concentration level that will produce effective antidepressant effects without causing any harmful or untoward side effects.

The compounds of the present invention may be administered for antidepressant purposes either as individual therapeutic agents or as mixtures with other therapeutic agents. Therapeutically, the instant compounds are generally given as pharmaceutical compositions comprised of an antidepressant amount of a compound of Formula I or a pharmaceutically acceptable salt and/or hydrate thereof and a pharmaceutically acceptable carrier. Pharmaceutical compositions which provide from about 1 to 750 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g. syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethylene glycol or silica) disintegrants (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection.

Such compositions having the desired clarity, stability and adaptability for parenteral use are obtained by dissolving from about 0.1% to 10% by weight of a Formula I compound or one of its salt forms in water or a vehicle consisting of a polyhydric aliphatic alcohol such as glycerine, propylene glycol, and the polyethylene glycols or mixtures thereof. The polyethylene glycols consist of a mixture of non-volatile, usually liquid, polyethylene glycols which are soluble in both water and organic liquids and which have molecular weights from about 200 to 1500.

When transnasal application is intended, the Formula I compound pharmaceutical composition is formulated in a pharmaceutical composition which enhances penetration of the nasal mucosa. Such formulations normally employ fatty acid salts of the Formula I base compound and their preparation and use would be known to one skilled in the pharmaceutical arts.

The general procedures for preparation of Formula I compounds are outlined in Schemes 1 and 2.

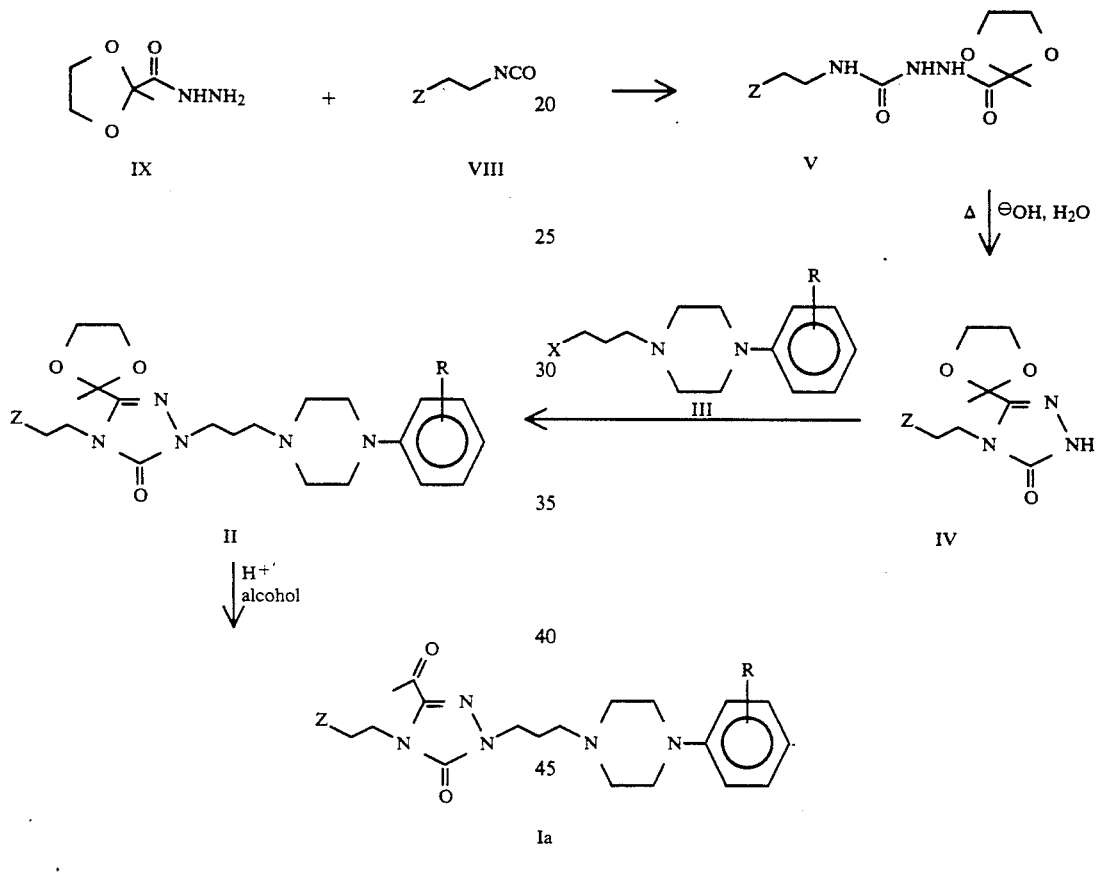

Scheme 1
Preparation of Formula Ia Compounds

In Scheme 1, the ethylene ketal of pyruvic acid hydrazide (IX), prepared by treating an alcoholic solution of the ethylene ketal of ethyl pyruvate with hydrazine hydrate; is reacted with an appropriate isocyanate (VIII) in toluene solution to provide the semicarbazide intermediate compound (V). The semicarbazide is ring-closed in aqueous hydroxide to provide the triazolone ketal (IV) which is alkylated at the 2-position of the ring with a phenylpiperazine of Formula III, such as 1-(3-chloropropyl)-4-(3-chlorophenyl)piperazine, to provide the ketal derivative (II). Hydrolysis of II in acidic media results in the product of Formula Ia.

Intermediate compound (III) is prepared according to the synthetic process disclosed in the nefazodone patent of Temple, Jr., et al., U.S. Pat. No. 4,338,317. This patent which has been referred to supra is hereby incorporated in its entirety by reference.

Scheme 2
Preparation of Formula Ib Compounds

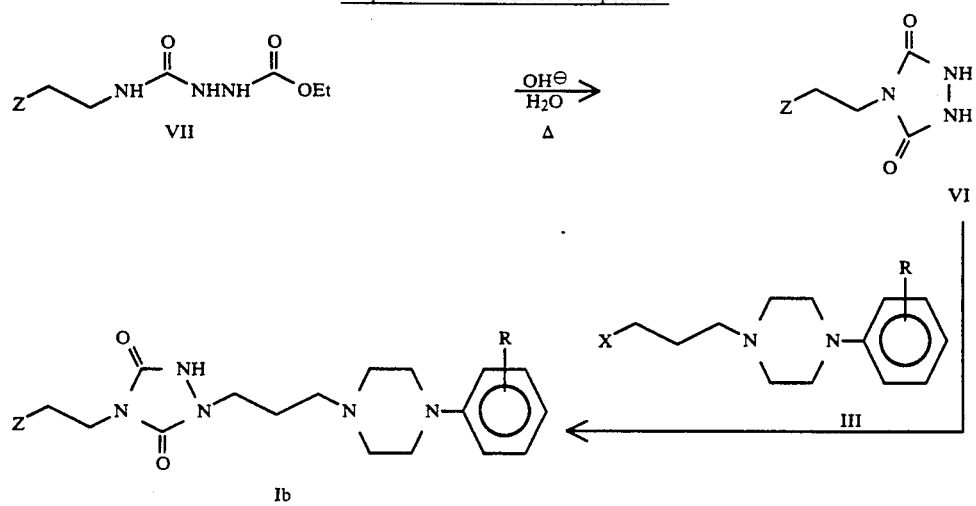

In Scheme 2, the semicarbazide of Formula VII, prepared by treating a toluene solution of an appropriate isocyanate (VIII) with ethyl carbazate; is ring-closed in aqueous hydroxide to give the 1,2,4-triazolidine-3,5-dione intermediate of Formula VI. Alkylation of VI with a phenylpiperazine (III), such as 1-(3-chloropropyl)-4-(3-chlorophenyl)piperazine provides the triazoldione product Ib. The formation of a bis-alkylated adduct was not a problem as its formation did not occur to any appreciable extent.

In both of these synthetic schemes, R and Z are the same as defined supra. The symbol X denotes an organic synthetic leaving group such as chloro, bromo, iodo, mesyl, tosyl, and the like; all of which are familiar to one skilled in organic synthesis. The starting materials used to prepare compounds VII and IX are common synthetic reagents and are commercially available or easily prepared according to well known procedures well known to those skilled in the pertinent art.

It should be appreciated that compound Ib could also be obtained by enzymatic (human liver microsomes) conversion of compound Ia in vitro. Administration of nefazodone or structural analogs to mammals will result in significant plasma levels of the related Ib compounds. By "significant plasma levels" is meant that these levels are from one to several-fold higher than those of the parent drug.

Regarding the molecular structure of compounds of Formula Ib, NMR spectral analysis indicates that these compounds exist almost completely in the dione form as opposed to the enol forms.

DESCRIPTION OF SPECIFIC EMBODIMENTS

The compounds which constitute this invention and their methods of preparation will appear more full from a consideration of the following examples which are given for the purpose of illustration only and are not to be construed as limiting the invention in sphere or scope. All temperatures are understood to be in degree C. when not specified.

The nuclear magnetic resonance (NMR) spectral characteristics refer to chemical shifts ($\delta$) expressed as parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), singlet (s), multiplet (m), doublet (d), doublet of doublets (dd), or quartet (q). Abbreviations employed are DMSO-$d_6$ (deuterodimethylsulfoxide). CDCl$_3$ (deuterochloroform), and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight.

Melting points were determined on a Thomas-Hoover melting point apparatus and are uncorrected. All $^1$H NMR spectra were recorded on a Brucker 360 MHz spectrometer using TMS as an internal standard. Thin layer chromatography (TLC) were carried out on precoated silica gel GF (250$\mu$) plates (Analtech) and visualized using UV light (254 nm). Flash chromatography was performed using finely divided silica gel (32-63$\mu$) obtained from ICN Biochemicals.

Synthesis of Intermediates

A. Intermediates For Synthesis of Ia Compounds

EXAMPLE 1

Ethylene Ketal of Pyruvic Acid Hydrazide (IX)

Ethyl pyruvate (5.09 g, 4.81 mL, 43 mmole) and ethylene glycol (5.39 g, 4.84 mL, 87 mmole) were combined in 4.5 mL benzene, to which p-toluenesulfonic acid monohydrate (113 mg) was added, and the resulting mixture was stirred at reflux temperature for 18 hr. with the water of reaction being collected in a Dean-Stark trap. Following concentration in vacuo, the residual yellow oil was taken up in 40 mL abs. ethanol, treated with hydrazine monohydrate (3.23 g; 3.13 mL; 65 mmol) and this reaction solution was heated at reflux for about 7 hr. Concentration in vacuo yielded a white solid which was recrystallized in about 20 mL isopropanol to provide, after drying in vacuo, crystalline product IX as 3.65 g (58%) of white needles, mp 120°-122°.

EXAMPLE 2

Phenoxyethyl semicarbazide intermediate (V)

A solution of sodium nitrite (9.90 g, 144 mmole) in 30 mL $H_2O$ was added dropwise over 6.5 min. to a well-stirred mixture of 3-phenoxypropionyl hydrazide hydrochloride (28.0 g, 129 mmole) in 155 mL $H_2O$ and 78 mL toluene being kept at 5° by ice-bath cooling. The temperature rose to 13°. After the temperature receded to 5° the mixture was stirred for an additional hr., Celite ® was added and the mixture was filtered through a Celite ® pad. The organic layer was separated and the aqueous phase was extracted with toluene (2×20 ml). The combined extracts were dried ($Na_2SO_4$) and filtered through a $MgSO_4$ pad. The toluene filtrate was slowly added dropwise, under a $N_2$ atmosphere, into a 250 mL 3-necked reaction flask sitting in an oil bath heated to 100°. The azide decomposed slowly and the toluene solution was stirred and heated until gas evolution ceased.

The isocyanate VIII solution was cooled to 18° and the pyruvic acid ketal hydrazide (IX; 18.9 g, 129 mmole) was added in one portion. The reaction mixture was stirred at ambient temperature for 16 hr. (during the first half-hour the reaction mixture temperature rose to 31° before subsiding). Solid precipitated during this time and the resulting thick mixture was cooled and filtered. The yellow solid was rinsed with additional toluene and dried in vacuo to yield 36.1 g (90.5%) of semicarbazide intermediate V, mp 103°–111°.

NMR spectral analysis was consistent with the desired product structure.

EXAMPLE 3

5-(2Methyl-1,4-dixolan-2yl)-4-(2-phenoxyethyl)-2,4-dihydro-3H-1,2,4-triazol-3-one (IV)

The phenoxyethyl semicarbazide intermediate V (30.5 g, 98.6 mmole; as prepared in Example 2) was introduced into a hot (95°) stirred solution of KOH (6.37 g of 87% KOH pellets, 98.6 mmole) in 600 mL $H_2O$ and stirred at gentle reflux for 6 hr. The mixture was filtered and the basic filtrate was cooled (ice bath) and neutralized (9.0 mL conc. HCl) and a yellow solid slowly precipitated during an additional 2 hr. of chilling and stirring. The mixture was filtered and the solid was rinsed with $H_2O$ and then dried in vacuo (over $P_2O_5$) to provide 14.07 g (49%) of Formula IV product, mp 142°–144°.

NMR spectral analysis was consistent with the desired structure.

EXAMPLE 4

2-(3-[4-(3-Chlorophenyl)-1-piperazinyl]propyl)-5-(2-methyl-1,4-dioxolan-2-yl)-2,4-dihydro-4-(2-phenoxyethyl)-3H-1,2,4-triazol-3-one (II)

The hydrochloride salt of 1-(3-chloropropyl)-4-(3-chlorophenyl)piperazine (III; 9.35 g; 30.2 mmole) was converted to the base form with 40% NaOH solution. Extraction of the basic aqueous liquid with $CH_2Cl_2$ and concentration in vacuo of the $CH_2Cl_2$ extracts gave 8.5 g of the base as an oil. The oil was combined with triazolone ketal intermediate IV (prepared in Example 3; 8.00 g, 2.75 mmole), $K_2CO_3$(11.4 g, 82.5 mmole) and KI (1.0 g) in 100 mL acetonitrile which was stirred at reflux for 24 hr. Filtration of the hot mixture and rinsing of the residue with additional acetonitrile gave a filtrate which was concentrated in vacuo to 16.3 g of a yellow orange viscous oil which was used as is for hydrolysis in the subsequent step.

B. Intermediates For Synthesis of Ib Compounds

EXAMPLE 5

1-Carbethoxy-4-(2-phenoxyethyl)semicarbazide (VII)

A solution of sodium nitrite (7.72 g, 0.112 mol) in deionized water (23.2 mL was added dropwise over 6.5 min. to a well stirred mixture of 3-phenoxypropionyl hydrazide hydrochloride[1] (22.00 g, 0.102 mol), deionized water (110 mL) and toluene (55 mL) that was cooled to 5° C. in an ice bath. The temperature rose to 13° C. After the mixture was stirred at 5° C. for one hr., Celite ® was added and the mixture was filtered through a pad of Celite ®. The organic layer was separated and the aqueous phase was extracted with toluene (2×20 mL). The combined extracts were dried over $Na_2SO_4$ and filtered through a pad of $MgSO_4$.
[1]Prepared according to U.S. Pat. No. 4,487,773, Example 5.

The clear, bright yellow toluene solution containing the intermediate azide was added dropwise, under a nitrogen atmosphere, to a 250 mL, 3-neck reaction flask setting in an oil bath that had been heated to 100° C. (oil bath temp.). The azide decomposed slowly and stirring and heating were continued until gas evolution ceased. The yellow isocyanate solution was then cooled to 15° C. and treated all at once with an equimolar amount (10.90 g, 0.102 mol) of ethyl carbazate. The resultant thick mixture was stirred at ambient temperature for one hour (temperature gradually rose to 33° C.) and the reaction was completed by heating to 90° C. (pot temp.). Finally the mixture was cooled to 10° C. and filtered. The product was rinsed with fresh toluene and dried in vacuo to yield 21.36 g (78%) of VII as a white solid; mp 170°–173° C. $^1H$ NMR (DMSO-$d_6$) was consistent.

Anal. Calcd for $C_{12}H_{17}N_3O_4$: C, 53.92; H, 6.41; N, 15.72. Found: C, 54.04; H, 6.37; N, 15.55.

EXAMPLE 6

4-(2-Phenoxyethyl)-1,2,4-triazolidine-3,5-dione (VI)

The 1-(ethoxycarbonyl)semicarbazide VII (10.28 g, 0.0385 mol) was added to a solution of potassium hydroxide (4.96 g, 0.0769 mol) in water (105 mL) and the suspension was stirred and heated in an oil bath at 95° C. (oil bath temp.) for one hour. The yellow mixture was cooled to 25° C. and filtered. The filtrate was further cooled in an ice bath and neutralized by the slow addition of 6.72 ml (0.0807 mol) of conc. HCl. After 15 min. a white precipitate of VI was collected by filtration, washed with water and dried to constant weight. Yield: 6.56 g (77%); mp 187°–189° C. $^1H$ NMR (DMSO-$d_6$,): δ=10.15 (s, 2H, equivalent NH's).

Anal. Calcd for $C_{10}H_{11}N_3O_3$: C, 54.29; H, 5.01; N, 19.00. Found: C, 54.23; H, 4.92; N, 18.60.

Synthesis of Formula I Products

A. Formula Ia

EXAMPLE 7

2-(3-[4-(3-Chlorophenyl)-1-piperazinyl]propyl)-5-acetyl-2,4-dihydro-4-(2-phenoxyethyl)-3H-1,2,4-triazol-3-one hydrochloride (Ia)

The ethylene ketal precursor (II; 14.50 g; 27.5 mmole) was dissolved in a mixture of 3N HCl (14 mL) and ethanol (100 mL) and heated at reflux for 4 hr. Progress of the reaction was monitored with TLC (silica gel; $CH_2Cl_2$/MeOH, 96:4). The reaction solution was concentrated in vacuo and the residue was partitioned between $H_2O$ (40 mL) and $CH_2Cl_2$ (50 mL). This mixture was made basic with 4N NaOH (12 mL) and the organic layer separated. The aqueous layer was extracted with a 30 mL portion of $CH_2Cl_2$. The combined $CH_2Cl_2$ portions were dried ($Na_2SO_4$) and concentrated to 16.5 g of crude Ia product as an oil which was purified by flash chromatography on silica gel (120 g of 32–63μ size) eluting with $CH_2Cl_2$-1% MeOH. The appropriate fractions were combined and concentrated to provide 8 g (59.9% yield from Compound IV) of the base as a gum.

The base was converted into a crystalline salt by taking up the gum in n-propanol (80 mL) and acidifying with 4N HCl (4.15 mL, one equivalent). Removal of the propanol and trituration of the residual solid in acetone provided a crystalline HCl salt which weighed 7.4 g after isolation and drying in vacuo ($P_2O_5$), mp 162°–165°.

NMR and IR spectral analyses conformed to the assigned structure.

Anal Calcd for $C_{25}H_{30}ClN_5O_3 \cdot HCl$: C, 57.69; H, 6.00; N, 13.46; Cl, 13.62. Found: C, 57.76; H, 6.10; N, 13.25; Cl, 13.90.

EXAMPLE 8

2-(3-[4-(3-Chlorophenyl)-1-piperazinyl]propyl)-4-(2-phenoxyethyl)-4H-1,2,4-triazole-3,5(1H,2H)-dione hydrochloride (Ib)

1-(3-Chloropropyl)-4-(3-chlorophenyl)piperazine hydrochloride (III) (13.58 g, 0.0438 mol) was suspended in water, layered with methylene chloride and made strongly basic with 40% aqueous NaOH while stirring and cooling in an ice bath. The organic layer was separated and the aqueous phase was extracted once more with methylene chloride. The combined extracts were washed once with water, dried ($Na_2SO_4$) and the solvent was evaporated to leave a clear amber oil.

A mixture of the triazolidine-3,5-dione (VI) (9.70 g, 0.0438 mol), the free base of (III) (11.96 g, 0.0438 mole) and pulverized sodium hydroxide pellets (1.75 g, 0.0438 mol) were combined in 2-propanol (340 mL) and heated at reflux for 3.5 hr. The mixture was filtered while hot and concentrated in vacuo to leave a cloudy amber oil. The crude product was then purified by flash chromatography on silica gel (225 g) using a gradient mixture of 2–4.5% methanol/methylene chloride as the eluent. Fractions containing pure product were identified by TLC (silica gel, 4% $CH_3OH/CH_2Cl_2$), combined and evaporated to dryness to yield 12.58 g (63%) of pale yellow gum.

The free base (12.58 g, 0.0274 mol) was dissolved in 2-propanol (175 mL) and treated with one equivalent of 2N HCl (13.70 mL). The salt quickly began to precipitate from solution. The mixture was cooled and filtered to yield 10.21 g (47%) of Ib as a white solid after drying in vacuo over $P_2O_5$; mp 201°–204° C. $^1H$ NMR (DMSO-$d_6$): δ=7.04 (s, 1H, NH).

Anal. Calcd for $C_{23}H_{28}N_5O_3 \cdot HCl$: C, 55.87; H, 5.91; N, 14.17; Cl, 14.34. Found (corrected for $H_2O$ and IPA): C, 56.13; H, 5.78; N, 14.24; Cl, 14.04.

We claim:
1. A compound of Formula I

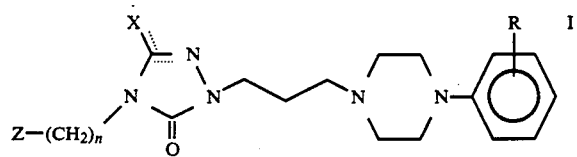

or a pharmaceutically acceptable acid addition salt and/or hydrate thereof wherein
R is halogen or trifluoromethyl;
X is oxygen or acetyl;
the single and dotted lines represent either a covalent single or double bond;
n is an integer from 2 to 4; and
Z is hydrogen or

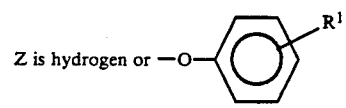

in which $R^1$ is hydrogen, halogen, $C_{1-4}$ alkoxy or trifluoromethyl.
2. The compound of claim 1 wherein X is acetyl.
3. The compound of claim 1 wherein X is oxygen.
4. The compound of claim 1 wherein Z is

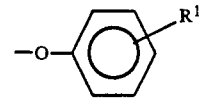

5. The compound of claim 1 wherein R is 3-chloro.
6. The compound of claim 4 wherein $R^1$ is hydrogen.
7. The compound of claim 2, 2-(3-[4-(3-chlorophenyl)-1-piperazinyl]propyl)-5-acetyl-2,4-dihydro-4-(2-phenoxyethyl)-3H-1,2,4-triazol-3-one hydrochloride.
8. The compound of claim 3, 2-(3-[4-(3-chlorophenyl)-1-piperazinyl]propyl)-4-(2-phenoxyethyl)-4H-1,2,4-triazole-3,5(1H,2H)-dione hydrochloride.
9. The antidepressant method which comprises administering to a mammalian host with depression, an effective antidepressant dose of a compound claimed in claim 1.
10. The antidepressant method which comprises administering to a mammalian host with depression, an effective antidepressant dose of a compound claimed in claim 7.
11. The antidepressant method which comprises administering to a mammalian host with depression, an effective antidepressant dose of a compound claimed in claim 8.
12. A pharmacological composition in unit dosage form suitable for systemic administration to a mammalian host comprising a pharmaceutical carrier and an effective antidepressant amount of a compound claimed in claim 1.
13. A pharmacological composition in unit dosage form suitable for systemic administration to a mammalian host comprising a pharmaceutical carrier and an effective antidepressant amount of a compound claimed in claim 7.
14. A pharmacological composition in unit dosage form suitable for systemic administration to a mammalian host comprising a pharmaceutical carrier and an effective antidepressant amount of a compound claimed in claim 8.

* * * * *